United States Patent [19]

Skarpness

[11] Patent Number: 4,538,472
[45] Date of Patent: Sep. 3, 1985

[54] PNEUMATIC CROSSCUT SAMPLER

[75] Inventor: Harold Skarpness, Minneapolis, Minn.

[73] Assignee: Gustafson, Inc., Dallas, Tex.

[21] Appl. No.: 518,646

[22] Filed: Jul. 29, 1983

[51] Int. Cl.³ .............................................. G01N 1/20
[52] U.S. Cl. ................................................. 73/863.55
[58] Field of Search ........... 73/863.51, 863.53, 863.54, 73/863.55, 863.56

[56] References Cited

U.S. PATENT DOCUMENTS

| | | | |
|---|---|---|---|
| 3,060,746 | 10/1962 | Gompper | 73/863.56 |
| 3,298,235 | 1/1967 | Platzer et al. | 73/863.54 |
| 3,393,567 | 7/1968 | Jirik . | |
| 3,474,675 | 10/1969 | Strand . | |
| 4,082,004 | 4/1978 | Weber et al. . | |
| 4,120,203 | 10/1978 | Clements | 73/863.54 |
| 4,170,900 | 10/1979 | Ozawa . | |

Primary Examiner—S. Clement Swisher
Attorney, Agent, or Firm—Palmtier, Sturm, Sjoquist & Baker, Ltd.

[57] ABSTRACT

A sampler for insertion in a flow duct carrying a stream of dry particulate material, including a housing with a sample head traversing the stream of flowing material and being movable within the head across the breadth of the stream of flowing material; a rotary disc in the bottom wall of the housing mounting the sample head; the mounting disc having a protective flange or ledge over the seal and thrust bearing at the periphery of the disc as to fully protect the seal and bearing ring against deteriorating effect of the particulate material; a sample spout extending through and rotatably mounted in the rotary mounting disc and being connected with the sample head for delivering samples of the material to the exterior of the housing; a rotary actuator for revolving the disc first in one direction and then the other; and a slide rod attached to the sample spout and moving through a slide block maintaining the sample head in predetermined upstream orientation facing the inlet of the housing.

18 Claims, 6 Drawing Figures

PNEUMATIC CROSSCUT SAMPLER

This invention relates to samplers for dry material flowing in a duct under significant pneumatic pressure.

BACKGROUND OF THE INVENTION

Crosscut samplers for dry material flowing under pneumatic pressure have not been unknown in the past.

Such a crosscut sampler is for the purpose of sampling the flow of dry particulate material flowing under pneumatic pressure in a flow duct, and in such a way that samples are taken at all different positions across the width of the stream of flowing materials in the duct. Such dry materials may flow with a unique characteristic in various types of ducts so that if the material flowing is not absolutely uniform, certain of the particles of certain sizes, or particles of certain density, may accumulate at one side or in one particular portion of the cross section of the flow duct; and unless a sample is acquired from all portions of the flowing stream of material, the sample may not be representative of the materials that are flowing.

In taking a crosscut sample of all of the materials flowing in the moving stream, numerous physical problems are encountered. Many of the dry materials which are carried in flow ducts under pneumatic pressure are extremely abrasive and any seals or bushings used in connection with a sampler are quickly eroded and deteriorated due to the continual abrading of the materials which are flowing. Depending on the design of the seals involved, certain of the types of materials which are being sampled will creep or migrate or be drawn into the seal, causing rapid deterioration.

Typical prior art includes U.S. Pat. No. 4,082,004 and 4,120,203.

SUMMARY OF THE INVENTION

An object of the invention is to provide a new and improved crosscut sampler which will operate reliably and accurately over a long service life and withstand the deteriorating effects of abrasive dry materials which are flowing in a duct and are being sampled.

Another object of the invention is to provide a novel crosscut sampler which will resist the deteriorating effects of abrasive dry flowing materials and will efficiently close the sampling head between periodic sampling cycles.

A feature of the present invention is a sampler with a housing which may be connected into the flow duct carrying the particulate material to be sampled. The sides of the housing are spaced outwardly of the flow stream. A sampling head or pelican has a narrow slotted side facing upstream and of sufficient length as to traverse the entire flow stream, and the sampling head moves entirely across the flow stream in a second direction perpendicular to the length of the slot. A closure panel in the housing and at one side of the flow stream is swingable to alternately close and open the material receiving slot in the side of the pelican.

The sampling head or pelican is swingably mounted on a peripheral portion of a rotary disc in one of the housing walls. The disc has a diameter wider than the flow stream as to carry the sampling head entirely across the flow stream.

The mounting for the pelican is the sample discharge tube which protrudes through the disc and is carried in a bearing thereon. Continuous upstream orientation of the pelican is maintained by an orienting arm secured on the discharge tube outside of the housing. The orienting arm is slidable in a positioning block which is also slidable transversely to the orienting arm and on a transverse rod affixed to the housing.

The rotary disc is rotatably turned through approximately a half revolution to traverse the pelican through the flow stream. Depending upon the size and frequency of the sample desired, the disc and pelican may be turned in only one direction in a single sampling cycle, or may be rotated first in one direction and then returned in the opposite direction to the home position in a sampling cycle.

The closure panel is swung simultaneously with commencing rotation of the disc, to open the slot in the sampling head. When a cycle is completed, the closure panel is again swung into closed position over the pelican.

The rotary disc may be driven by a pneumatic rotary actuator or by another form of double acting cylinder, mechanically driving the disc.

The sampler provides the advantage that abrasive dry material flowing in the duct and being sampled will not interfere with the functioning of the sampler. The pelican is confined by the closure panel as to prevent deterioration of the pelican and to prevent migration of unwanted material into the pelican and sampling tube.

DETAILED SPECIFICATION

Figure 1:
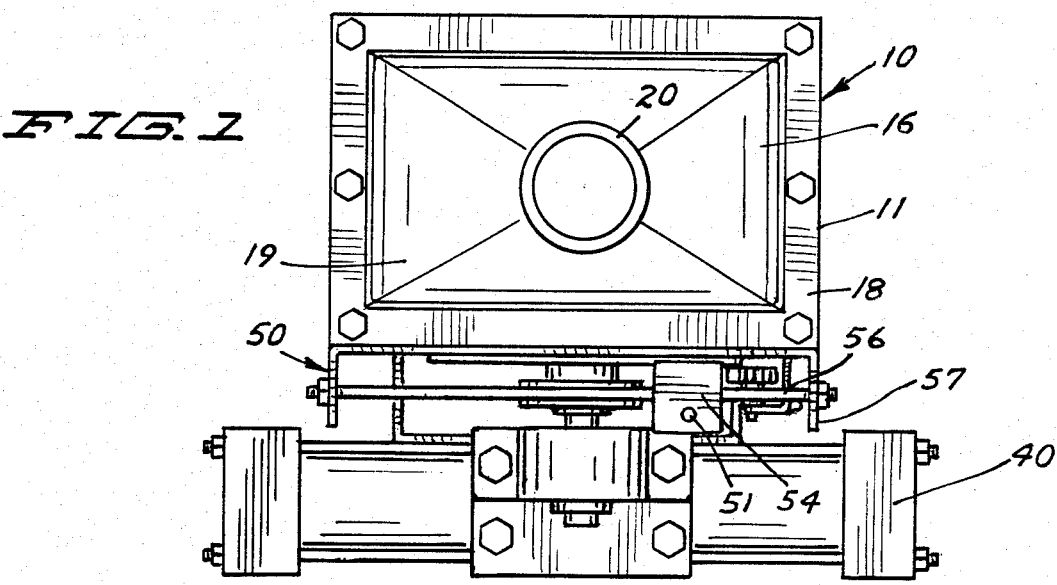
FIG. 1 is an end elevation view of the sampler.

One form of the crosscut sampler is illustrated in the drawings and is indicated in general by numeral 10. The sampler includes a housing 11 with upright sidewalls 12 and 13 and top and bottom walls 14 and 15. The sidewalls and top and bottom walls are secured to each other in fixed relation by machine screws through the top and bottom walls and into the side edges of the upright sidewalls 12 and 13. The housing 11 also includes duct adapters 16 and 17 with mounting flanges 18 connected by machine screws to the ends of the wall panels 12–15. The adapters 16 and 17 also have funnels or cone shaped sections 19 connecting the mounting flanges 18 with duct receiving sleeves 20 which fit onto the flow ducts 21 into which the sampler 10 is to be mounted.

Flow of material through the ducts 21 is indicated by the arrows 22; and the connector sleeves 20 of the housing define the flow passage P through the housing 11.

The bottom wall 15 of the housing has a circular opening 23 therein. The wall 15 also has an inwardly protruding annular flange or ledge 24 around the periphery of the opening 23 and adjacent the lower face of the wall 15.

A rotary disc 25 is supported in the circular opening 23 of the bottom wall 15 so that the inner surface 25.1 of the disc lies flush with the inner face 15.1 of the wall.

The disc 25 has an annular ledge or flange 26 immediately adjacent the inner surface 25.1 of the disc; and the disc 25 also has a second annular ledge or flange 27 protruding from its periphery at a location intermediate the thickness of the disc 25. The outer peripheries of both of the annular ledges 26 and 27 are in close fitting relation with the circular opening 23 to minimize the likelihood of particulate material collecting between the disc and the periphery of the opening in the wall.

The annular recess 28 in the periphery of the circular disc 25 confines the seal ring 28.1 which seals against both the inner periphery of the opening 23 and against the disc 25 in the recess 28. The seal ring 28.1 is formed of elastomeric material such as rubber and has a generally U-shaped cross section, with the open side of the U facing the ledge 26 and facing in the general direction of the interior of the housing 11.

A recess space 29 at the periphery of disc 25 between the ledge 27 of the disc and ledge 24 of the housing wall 15, confines a nylon annular bearing ring 30 which maintains the position of disc 25 in relation to the wall 15 as to maintain the inner faces 25.1 and 15.1 flush with each other. The bearing provided by nylon ring 30 may be of other plastic materials, or may take other forms, such as ball bearings confined in raceways machined into ledges 24 and 27.

The disc 25 also carries an outer rigid disc retainer plate 31. In the form illustrated, the disc plate 31 is formed of a fiber material, and the periphery of it lies against the ledge or flange 24 of the housing wall 15. The disc plate 31 is affixed to the disc 25 and functions to retain the disc 25 in predetermined relation with the housing wall 15. The disc plate 31 is affixed to the disc by machine screws 32.

A drive shaft 33 is inserted into a tapped aperture 34 at the center of disc 25. A sprocket 34 is affixed as by bolts 35 to the mounting plate 36 which lies against the disc plate 31 and is also clamped by machine screws 32 to the disc 25. Rotary power is supplied to the sprocket 34 by chain 37 driven from a sprocket 38 at the output shaft 39 of a pneumatic rotary actuator 40. The pneumatic rotary actuator 40 will revolve the sprocket 38, first in one direction during one phase of an operating cycle; and then will drive the sprocket 38 in the opposite direction so as to first turn disc 25 in one direction and then turn it in the opposite direction. Operation may be phased as to turn the disc 25 through 180°, at which time the disc may be stopped until the start of another operating cycle; alternately, the disc may be staged to operate first in one direction through 180° and immediately be returned to the rest position, without hesitation, by suitable control of the rotary actuator 40. It has been found convenient, in the present use of the sampler 10, that the disc 25 should be oscillated first in one direction and then return to its home or rest position in each cycle of operation. Also, other forms of drive mechanisms may be substituted for the rotary actuator. For instance, other forms of pneumatic cylinders may be used to drive the disc; and in certain environments, electric motors may be suitable, or rotary hydraulic motors may also be useful.

A sample head or pelican 41 is confined within the interior of the housing 11. The sample head is hollow, with an open interior 42. Sample head 41 has a slot-like opening 43 at its narrow side 44 to face upstream to the inlet end of the housing. The slot-like opening 43 traverses the entire width of the flow passage P through the housing. The sample head 41 is movable across the breadth of the flow passage, in the direction indicated by arrows a and b in FIG. 5 so as to be movable entirely through the flow passage and to collect samples from all portions of the flow passage.

The sample head 41 is mounted on a rotary sample spout or tube 45 which extends through and is rotatably mounted upon a peripheral portion of the rotary disc 25 in the bottom housing wall. The open interior 42 of the sample head is in open communication with the interior of the sample spout or tube 45 so as to continuously discharge the samples of material being collected to the exterior of the housing. A sample collecting container, such as a bag, may be connected onto the end of the spout 45; or alternately, a flexible hose or duct may be connected between the spout 45 and a stationary container so as to collect the sample of material from the sample head.

The disc 25 has an opening 46 therein which receives the spout 45 and its outwardly protruding annular flanges 47 and a seal 48, together with a bushing 49 which supports the spout 45 in the disc opening 46. It will be seen that the flange 47 on the spout 45 also lies flush with the inner surface 25.1 of the disc.

The sampler 10 is provided with orienting means 50 for maintaining the head 41 in predetermined orientation within the housing as to continuously cause the slot-like entrance port 43 to face upstream toward the inlet end of the housing. The orienting means include a rigid slide bar threaded into and affixed to a rigid collar 52 which is keyed by a set screw onto the sample spout 45. The slide rod 51, in the form illustrated, lies parallel to the sample head 41 and extends, from the collar 52, in a direction parallel and upstream of the flow passage. The slide rod 51 extends through a bearing aperture 53 in a slide block 54. The slide rod 51 is free to slide longitudinally through the bearing aperture 53. Slide block 54 has a second bearing aperture 55 through it, through which extends a stationary mounting rod 56. The mounting rod 56 is affixed into mounting brackets 57 at the sides of the bottom wall 15 of the housing.

Figure 5:
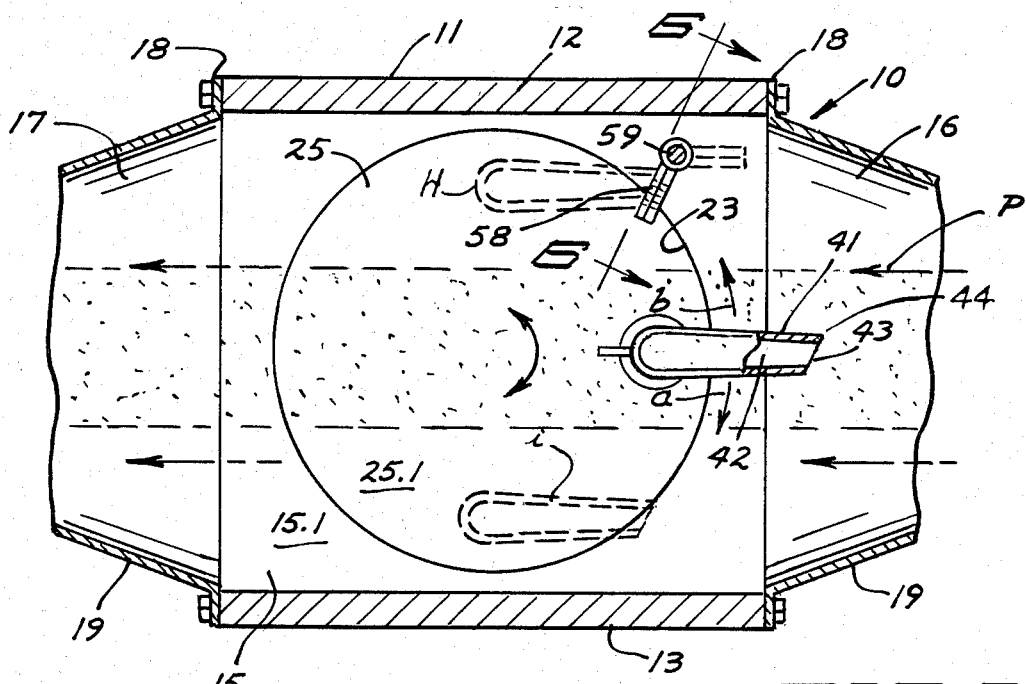
FIG. 5 is an enlarged detail section view taken approximately at 5—5 of FIG. 4.
Figure 6:
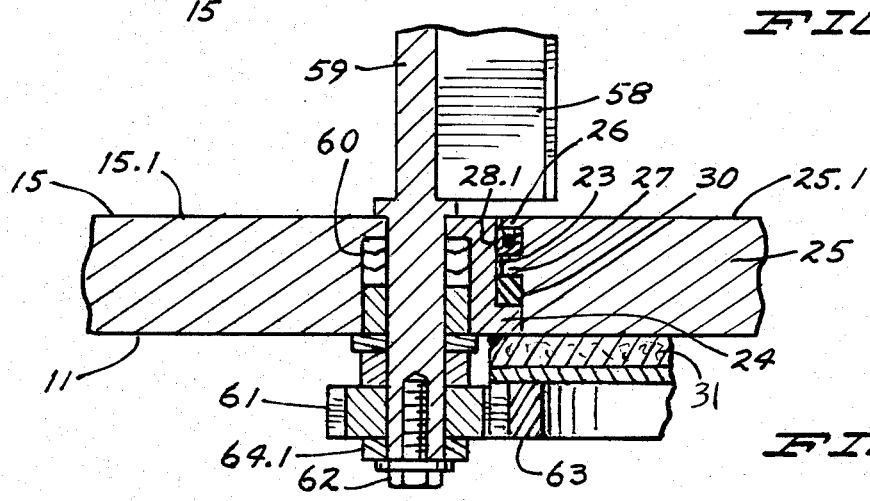
FIG. 6 is an enlarged detail section view taken approximately at 6—6 of FIG. 5 and with the closure panel swung to the dotted line position of FIG. 5.
Figure 2:
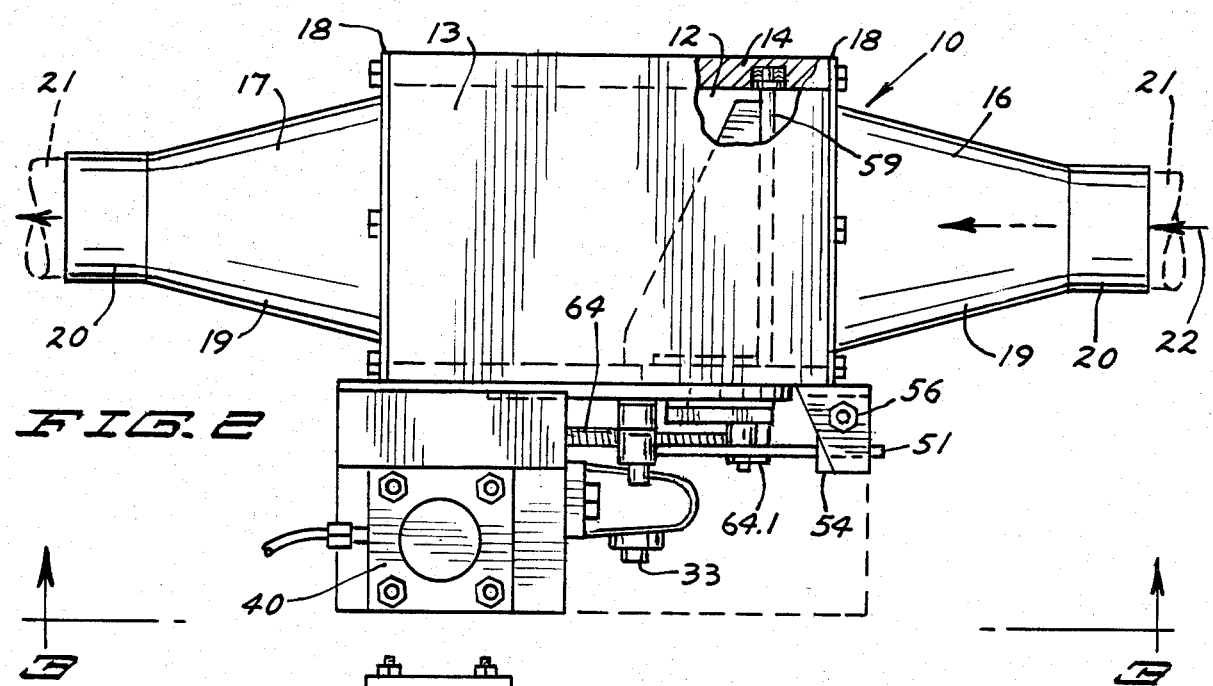
FIG. 2 is a side elevation view of the sampler.
Figure 3:
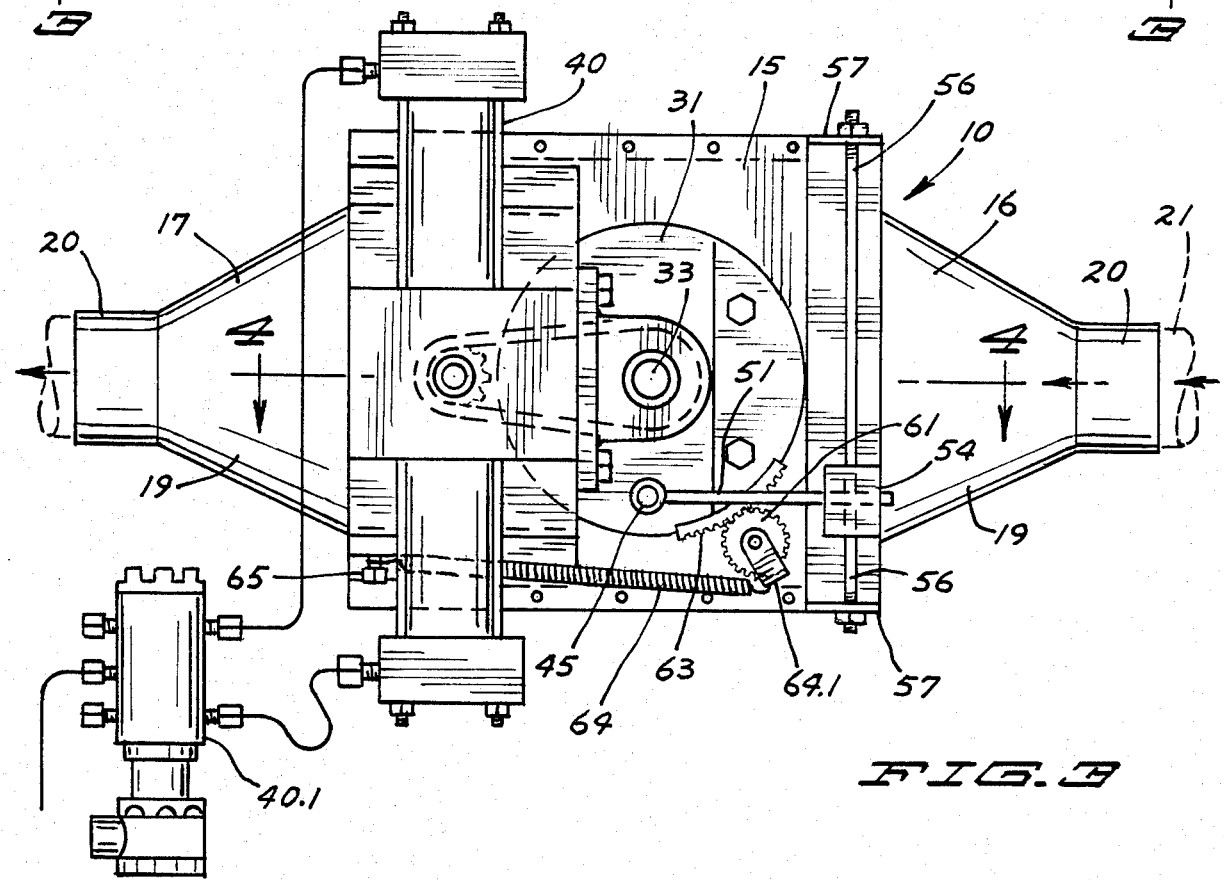
FIG. 3 is a bottom plan view of the sampler, together with a diagrammatic illustration of the pneumatic connections therefor.
Figure 4:
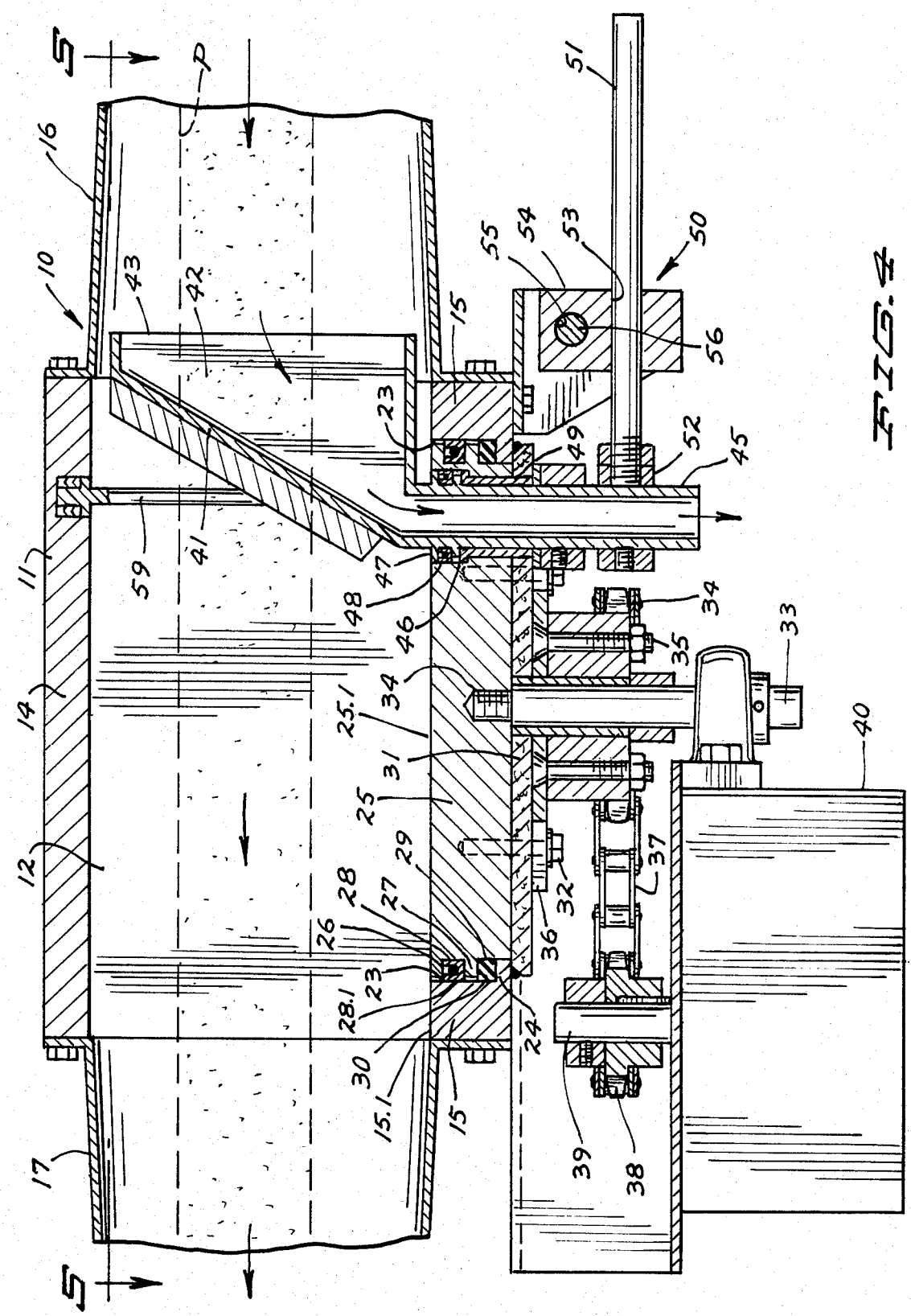
FIG. 4 is an enlarged longitudinal section taken approximately at 4—4 of FIG. 3.

An elongate closure panel 58 extends upwardly through the interior of housing 11, adjacent the periphery of disc 25 to close against the end edge and access slot 43 when the sample head 41 is in its home position indicated by the letter H in FIG. 5. The closure panel 58 is swingably mounted with a rotary mounting rod 59 which traverses the entire height of the interior of the housing and has its opposite ends rotatably mounted in the top and bottom walls 14 and 15. The shaft 59 extends through an opening in the bottom wall 15 of the housing, and is confined and mounted in a suitable bushing 60 therein. The outer end of the shaft 59 has a pinion gear 61 affixed thereon, as by machine screw 62. The gear 61 is meshed with an arcuate gear rack 63 which is affixed to and extends along a portion of the periphery of the disc plate 31 and along the periphery of disc 25. The pinion 61 and rack 63 function to turn the shaft 59 and swing the closure panel 58 out of confronting relation with the sample head 41 when the disc 25 commences turning; and then when the closure panel 58 has swung to the open position illustrated in full lines in FIG. 5, a spring 64 will retain the closure panel 58 in its open position as the pinion 61 turns off the end of the rack 63 which revolves with the disc 25. When the disc 25 and sample head 41 return to its home or rest position H illustrated in FIG. 5, the rack 63 again meshes with the pinion 61 to turn the pinion and swing the closure panel 58 into confronting and closing relation with the slotted narrow side of the sample head. The spring 64 will be seen to be attached to a lever arm 64.1 clamped to the pinion 61; and an anchor screw 65 affixed to the housing.

In operation, the sampler 10 will be operated periodically to obtain a sample of the particulate material flowing through the duct 21 and through the flow passage P in the housing 11. Suitable switching or valving is operated to control the operating valve 40.1 for the pneumatic actuator 40 which is operated first in one direction and then in the other direction to turn the disc 25 through approximately 180° in a first direction and then returning the disc 25 to its rest or home position. As the disc 25 commences movement, the rack 63 revolves the pinion 61 which causes the closure panel 58 to swing away from the end of the sample head 41, whereupon the sample head is free to start its movement with the periphery of the disc 25. The slot-like entrance port 43 of the head is sufficiently long to extend vertically across the flow passage P; and the revolving of the disc 25 and sample head 41 moves the sample head horizontally through the breadth of the flow passage so that samples of the particulate material from all portions of the flow passage are collected in the sample head 41. The sample head 41 will move entirely to the opposite side of the housing to the intermediate position i as seen in FIG. 5, and then the rotary actuator 40 will reverse, to reverse the direction of rotation of the disc 25 and the sample head will again move through the flow passage and the stream of flowing particulate material and will be returned to its home position H, whereupon the closure panel 58 will swing against the end of the sample head to again close the head and prevent any stray material from entering the sample head. Thereupon, the rotary actuator 40 will stop and wait until the valve 40.1 is again operated to start another cycle.

During the cycle of operation, the position of the head 41 is controlled by the orienting mechanism 50. As the disc 25 causes the head 41 to traverse through the stream of flowing material, the slide rod 51 will move the slide block 54 along the guide rod 56; and simultaneously, the slide rod 51 slides through the slide block 54. The result is that the guide rod 51 and the sample head 41 are retained precisely in the same longitudinal position as to continue the slot-like entrance port 43 in an upstream position, facing the inlet of the housing, and thereby accepting sample quantities of the particulate material flowing in the stream of material. As the sample head 41 is retained in its upstream facing position, the sample spout 45 revolves with respect to the disc 25.

It is important to note that the disc 25 and the sample head 41 are supported on the bottom wall 15 of the housing, at the flanges 24 and 27 and the nylon bearing ring 30 therebetween. The spacing between the flange 26 of the disc and the inner periphery of the circular opening 23 in the bottom wall 15 is minimal as to minimize any possibility of dry particulate material collecting in this space. The seal 28.1 retains the pneumatic air pressure in the housing 11, without allowing escape of such pressure. Because the inner surface 25.1 of the disc lies substantially flush with the inner face 15.1 of the bottom wall 15, the likelihood of any particulate material collecting between the disc and the circular opening 23 is minimized.

Similarly, the flange or ledge 47 on the periphery of the sample spout 45 lies flush with the inner face 25.1 of the disc as to minimize any possibility of particulate material collecting in this rotary bearing area.

It will be seen that the present invention facilitates the taking of a crosscut sample of the stream of flowing material through the housing 11. Because the particulate material cannot find its way into the seal between the edge of the disc and the inner periphery of the opening in the housing wall, the particulate material will not cause the deteriorating effect of wear in this sampler. Similarly, the sampling slot of the sample head is closed and covered at the end of each cycle of operation by the closure panel and will not be subject to damage and the deteriorating effect of flowing particulates between the times during which samples are taken. The sample head 41 is continuously maintained in its upstream facing position by the orienting slide rod 51 acting through the guide block 54.

What is claimed is:

1. A crosscut sampler for particulate material flowing under pneumatic pressure in a duct comprising,
   a housing for connection into the duct and having an inlet and an outlet and a flow passage therebetween for the stream of flowing material, the housing having a wall with an inner face lying along the flow passage and also having a circular opening therein,
   a sample head in the housing and having a slotted sample receiving side facing upstream and traversing the flow passage for collecting samples of the flowing material, and
   a circular mounting disc in the circular wall opening and having means mounting the head for moving the slotted side transversely across the flow passage and the stream of flowing material, the disc having an inner face lying flush with the inner face of the housing wall, and seal means between the periphery of the disc and the housing wall.

2. A crosscut sampler according to claim 1 and orienting means connected with the head and maintaining the slotted side facing the inlet of the housing.

3. A crosscut sampler according to claim 1 and a sample delivery spout connected with the sample head and extending through the rotary disc and to the exterior of the housing for delivering the samples collected.

4. A crosscut sampler according to claim 3 and the delivery spout being rotatable on the disc.

5. A crosscut sampler according to claim 3 and the delivery spout being on a peripheral portion of the disc and being rotatable with respect to the disc.

6. A crosscut sampler according to claim 5 and coordinating means between the housing and the spout and turning the spout and head in response to disc rotation to maintain the sample receiving side of the head facing upstream of the flow passage.

7. A crosscut sampler according to claim 1 and the peripheries of the circular disc and wall confronting each other in close fitting relation and confining the seal means against abrading by the flowing material.

8. A crosscut sampler according to claim 7 wherein the housing wall and the mounting disc have inner sides adjacent the flow passage and outer sides, the mounting disc having a confining ledge around its periphery and at the inner side of the disc, the housing wall having supporting ledge at the periphery of the circular opening and spaced from the inner side of the housing wall to underlie the peripheral ledge of the disc.

9. A crosscut sampler according to claim 7 wherein said housing being oriented with said wall and the circular opening therein disposed below the flow passage, the mounting disc being below the sample head and flow passage, and means accommodating downward flow of material from the sample head and through the mounting disc.

10. A crosscut sampler for particulate material flowing in a duct, comprising
- a housing for connection into the duct and having an inlet and an outlet and a flow passage therebetween for the stream of flowing material
- a sample head in the housing and having a slotted sample receiving side facing upstream and transversing the flow passage for collecting samples of the flowing material,
- movable means in the housing and mounting the sample head for moving the slotted side transversely across the flow passage and the stream of flowing material, and
- a head closing panel in the housing at one side of the flow passage and being swingable into and out of confronting relation to the upstream side of the head.

11. A crosscut sampler for particulate material flowing in a duct, comprising
- a housing for connection into the duct and having an inlet and an outlet and a flow passage therebetween for the stream of flowing material, the housing having a wall lying along and spaced from the flow passage, the wall having a circular opening therein,
- a sample head in the housing and having a slotted sample receiving upstream side facing the inlet of the housing and traversing the width of the flow passage for collecting samples of flowing material, the sample head being movable transversely of the slot to move across the breadth of the flow passage in order to collect samples of particulate material from all portions of the flow passage,
- a circular rotary mounting disc in the circular wall opening and having an inner face lying substantially flush with the inner surface of the housing wall, means to rotate the disc in the wall,
- a sample spout connected to and mounting said sample head, the sample spout extending through and being rotatable in said mounting disc in spaced relation with the rotation axis of the mounting disc,
- a swinging closure panel in the housing at one side of the flow passage and adjacent the periphery of the disc, the closure panel being swingable on an axis lying parallel to the disc axis and being swingable into and out of obstructing relation with the slotted side of the sample head,
- a drive connection between the disc and the closure panel to coordinate the swinging of the panel with the rotation of the disc and with the sample head, and
- sample head orienting means maintaining the slotted side of the sample head facing upstream and the inlet of the housing.

12. A crosscut sampler according to claim 11 wherein the housing wall and mounting disc having ledges at the disc and opening peripheries and in confronting relation with each other, and sealing means between said ledges.

13. A crosscut sampler according to claim 7 and the circular disc having a groove in the periphery of the disc and spaced from the inner face of the disc to define an annular confining flange in said close fitting relation to the periphery of the wall, and the seal means being disposed in said groove.

14. A crosscut sampler according to claim 7 and the wall having a peripheral support ledge spaced from the inner face and protruding inwardly of the opening, a bearing ring on the ledge and engaging the periphery of the mounting disc, and the mounting disc having outwardly protruding peripheral ledge means between the bearing ring and the inner face of the disc, and said ledge means and the disc being, supported on the bearing ring, and said ledge means having said close fitting relation with the periphery of the wall adjacent said inner face to keep the flowing material from between the peripheries of the disc and wall.

15. A crosscut sampler according to claim 14 and the wall and disc also having outer sides outer sides opposite said inner faces, and means engaging said outer sides of the disc and wall and maintaining the disc in supported relation on the support ledge and bearing ring.

16. A crosscut sampler according to claim 15 and said retaining means comprising a disc plate on the mounting disc and protruding outwardly into lapped relation with the outer side of the wall adjacent the opening.

17. A crosscut sampler according to claim 10 and means coordinating swinging of the head closing panel into and out of confronting relation with the upstream side of the head, with the transverse movement of the head across the flow passage.

18. A crosscut sampler according to claim 17 and said mounting means being rotatable to swing the sample head through an arc and transversely across the flow passage and stream of following material, and orienting means connected with the head and maintaining the slotted side facing the inlet of the housing.

* * * * *

UNITED STATES PATENT AND TRADEMARK OFFICE
CERTIFICATE OF CORRECTION

PATENT NO. : 4,538,472
DATED : September 3, 1985
INVENTOR(S) : Harold Skarpness

It is certified that error appears in the above-identified patent and that said Letters Patent are hereby corrected as shown below:

Column 6, line 33, after "circular" and before "mounting", insert --rotary--.

Signed and Sealed this

Third Day of December 1985

[SEAL]

Attest:

Attesting Officer

DONALD J. QUIGG

Commissioner of Patents and Trademarks